(12) United States Patent
Small et al.

(10) Patent No.: US 6,680,055 B1
(45) Date of Patent: Jan. 20, 2004

(54) MYCOLACTONE AND RELATED COMPOUNDS, COMPOSITIONS AND METHODS OF USE

(75) Inventors: Pamela L. C. Small, Knoxville, TN (US); Kathleen M. George, Missoula, MT (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/980,063

(22) PCT Filed: Jun. 2, 2000

(86) PCT No.: PCT/US00/15428

§ 371 (c)(1),
(2), (4) Date: Feb. 27, 2002

(87) PCT Pub. No.: WO00/75126

PCT Pub. Date: Dec. 14, 2000

Related U.S. Application Data

(60) Provisional application No. 60/137,367, filed on Jun. 3, 1999.

(51) Int. Cl.[7] .......................... A61K 39/00; A61K 31/70; C12Q 1/24; C07H 1/00; C07D 313/00
(52) U.S. Cl. ..................... 424/184.1; 424/168.1; 435/30; 435/72; 435/124; 435/253.1; 514/23; 514/28; 514/450; 536/1.11; 536/7.1; 536/18.7; 549/266
(58) Field of Search ................... 536/7.1, 1.11, 536/18.7; 514/450, 30, 23, 28; 424/168.1, 184.1; 435/28, 72, 124, 233.1, 30, 253.1; 549/266

(56) References Cited

FOREIGN PATENT DOCUMENTS

WO   WO 98 50576 A   11/1998

OTHER PUBLICATIONS

George et al., "Partial Pruification and Characterization of Biological Effects of a Lipid Toxin Produced by *Mycobacterium ulcerans*," Infection and Immunity, vol. 66, No. 2, 587–593 (Feb. 1998).
George et al., "Mycolactone A Polyketie Toxin from *Mycobacterium ulcerans* Required for Virulence," Science, vol. 283, No. 2, 5403, 854–857 (Feb. 1999).
George et al., "A *Mycobacterium ulcerans* Toxin, Mycolactone, Causes Apoptosis in Guinea Pig Ulcers and Tissue Culture Cells," Infection and Immunity, vol. 68, No. 2, 877–883 (Feb. 2000).
Gunawardana et al., "Characterization of Novel Macrolide Toxins, Mycolactones A and B, from a Human pathogen, *Macobacterium ulcerans*," Journal of the American Chemical Society, vol. 121, No. 25, 6092–6093 (Jun. 1999).
Hockmeyer et al., "Further Characterization of *Mycobacterium ulcerans* toxin ," Infect Immun, vol. 21, No. 1, 124–128 (Jul. 1978).

Pahlevan et al., "The Inhibitory Action of *Mycobacterium ulcerans* Soluble Factor on Monocyte/T–Cell Cytokine Production and NF–kb Function," Journal of Immunology, vol. 163, No. 7, 3928–3935 (Oct. 1999).
Pimsler et al., "Immunosuppresive Properties of the Soluble Toxin from *Mycobacterium ulcerans*," Journal of Infectious Diseases, vol. 157, No. 1, 577–580 (Jan. 1998).
Read et al., "Cytotoxic activity of *Mycobacterium ulcerans*," Infect Immun, vol. 9, No. 6, 1114–1122 (Jun. 1974).

*Primary Examiner*—Elli Peselev
(74) *Attorney, Agent, or Firm*—Leydig, Voit & Mayer, Ltd.

(57) ABSTRACT

The present invention provides, inter alia, polyketide macrolides including a polyketide macrolide of the structure wherein $R^1$–$R^5$ are the same or different and each is independently selected from the group consisting of hydrogen, $R^6$, a $C(O)R^7$, a $C(S)R^7$, a $C(O)NHR^7$, and a $C(S)NHR^7$, each occurrence of $R^6$ is independently selected from the group consisting of a $C_1$–$C_6$ alkyl, a $C_5$–$C_{12}$ aryl, and a sugar, each occurrence of $R_7$ is independently selected from the group consisting of hydrogen, a $C_1$–$C_6$ alkyl, and a $C_5$–$C_{12}$ aryl, and wherein $R^1$ and $R^2$, $R^2$ and $R^3$, and/or $R^4$ and $R^5$ can be taken together to form a ketal ring. Also provided are aseptic mixtures of polyketide macrolides isolated from *M. ulcerans* in a pharmaceutically acceptable carrier, methods of using the polyketide macrolides and aseptic mixtures to inhibit cancer and suppress an inflammatory response in a mammal, a method of inducing an immune response to *Mycobacteria ulcerans* without inducing a buruli ulcer, and a composition comprising *M. ulcerans*.

28 Claims, No Drawings

MYCOLACTONE AND RELATED COMPOUNDS, COMPOSITIONS AND METHODS OF USE

This application is a U.S. national phase of PCT/US00/15428, which was filed on Jun. 2, 2000, and which claims the benefit of U.S. provisional patent application No. 60/137,367, which was filed on Jun. 3, 1999.

TECHNICAL FIELD OF THE INVENTION

The present invention relates to pharmacoactive polyketide macrolides obtained from *M. ulcerans*, semi-synthetic derivatives thereof, aseptic mixtures of polyketide macrolides obtained from *M. ulcerans.* and methods of using the same.

BACKGROUND OF THE INVENTION

*Mycobacteria ulcerans* is the causative agent of buruli ulcers. Buruli ulcers are progressive necrotic skin lesions that can persist for decades without treatment and which are not uncommonly suffered by persons living in tropical climates, including parts of Africa. Buruli ulcers are painless, not accompanied by symptoms of systemic disease, and are generally not accompanied by an initial acute inflammatory response. Several articles have shown evidence that *M. ulcerans* produces a toxin, although the identity of this toxin or toxins has heretofore remained unknown. Read et al., *Infect. Immun.*, 9, 1114 (1974), reported that the sterile filtrate of an *M. ulcerans* liquid culture has cytopathic activity on cultured murine fibroblasts. Pimsler et al., *J. Infect. Dis.*, 157, 577 (1988), reported that the sterile filtrate of an *M. ulcerans* has an immunosuppressive property. George et al., *Infect. Immun.*, 66, 587–593 (1998), reported that a lipid toxin that is soluble in acetone could be isolated from *M. ulcerans* culture supernatant by organic extraction and causes a cytopathic effect by arresting L929 murine fibroblasts in the $G_I$ phase of the cell cycle.

SUMMARY OF THE INVENTION

The present invention provides a polyketide macrolide that can be isolated from virulent cell cultures of *Mycobacterium ulcerans*. The inventive polyketide macrolide has the formula of formula 1:

(Formula 1)

Also provided are pharmacologically acceptable derivatives and prodrugs of the polyketide macrolide of Formula 1.

Suitable pharmacologically acceptable esters, ethers and prodrugs of the polyketide macrolide include those of Formula 2:

(Formula 2)

wherein $R^1$–$R^5$ are the same or different and each is independently selected from the group consisting of hydrogen, $R^6$, a $C(O)R^7$, a $C(S)R^7$, a $C(O)NHR^7$, and a $C(S)NHR^7$, each occurrence of $R^6$ is independently selected from the group consisting of a $C_1$–$C_6$ alkyl, a $C_5$–$C_{12}$ aryl, and a sugar, each occurrence of $R_7$ is independently selected from the group consisting of hydrogen, a $C_1$–$C_6$ alkyl, and a $C_5$–$C_{12}$ aryl, and wherein $R^1$ and $R^2$, $R^2$ and $R^3$, and/or $R^4$ and $R^5$ can be taken together to form a ketal ring.

The present invention also provides an aseptic mixture of macrolides comprising (i) a polyketide macrolide isolated from *Mycobacteria ulcerans* wherein the fraction corresponding to the distance the polyketide macrolide travels from the origin divided by the distance the solvent front travels past the origin (Rf) is greater than 0.15 and less than 0.60 when chromatographically separated by silica-gel thin-layer-chromatography employing a solvent system of 90:10:1 of chloroform:methanol:water and (ii) a pharmaceutically acceptable carrier.

The present invention further provides methods of using a polyketide macrolide to inhibit cancer in a mammal and to suppress an inflammatory response in a mammal. These methods comprise administering an effective amount of an isolated polyketide macrolide or an aseptic mixture of macrolides to the mammal so as to inhibit cancer or to suppress an inflammatory response, respectively.

Further provided is a method of inducing an immune response to *Mycobacteria ulcerans* without inducing a buruli ulcer. The method comprises inoculating a mammal with an immune response-inducing amount of *M. ulcerans* cells that produce less than about 5% of polyketide macrolides per cell in comparison to a fresh culture of a virulent isolate of *M. ulcerans* 1615, wherein said polyketide macrolides have an Rf of greater than 0.15 and less than 0.60 when chromatographically separated by SG-TLC employing a solvent system of 90:10:1 of chlorform:methanol:water. The mammal has an immune response to *M. ulcerans* and does not develop a buruli ulcer.

Still further provided is a composition comprising *M. ulcerans* cells that produce less than about 5% of polyketide macrolides per cell in comparison to a fresh culture of a virulent isolate of *Mycobacteria ulcerans*, wherein the polyketide macrolides have an Rf of greater than 0.15 and less than 0.60 when chromatographically separated by SG-TLC employing a solvent system of 90:10:1 of chloroform:methanol:water.

DETAILED DESCRIPTION OF THE INVENTION

The present invention provides an isolated polyketide macrolide that can be isolated from virulent isolates of *Mycobacterium ulcerans*. The polyketide macrolide has the formula of Formula 1:

(Formula 1)

Also provided are pharmacologically acceptable derivatives and prodrugs of the polyketide macrolide of Formula 1.

Suitable pharmacologically acceptable esters, ethers and prodrugs of the polyketide macrolide include those of Formula 2:

(Formula 2)

wherein $R^1$–$R^5$ are the same or different and each is independently selected from the group consisting of hydrogen, $R^6$, a C(O)$R^7$, a C(S)$R^7$, a C(O)NH$R^7$, and a C(S)NH$R^7$, each occurrence of $R^6$ is independently selected from the group consisting of a $C_1$–$C_6$ alkyl, a $C_5$–$C_{12}$ aryl, and a sugar, each occurrence of $R^7$ is independently selected from the group consisting of hydrogen, a $C_1$–$C_6$ alkyl, and a $C_5$–$C_{12}$ aryl, and wherein $R^1$ and $R^2$, $R^2$ and $R^3$, and/or $R^4$ and $R^5$ can be taken together to form a ketal ring. For example, $R^1$ and $R^2$ can be taken together as a $C_1$–$C_6$ alkyl. Suitable sugars in the context of the present invention include, but are not limited tetroses, pentoses, hexoses, heptoses, and disaccharides and polysaccharides comprising tetroses, pentoses, hexoses, and heptoses. Suitable aryl substituents of the present invention include heteroaryl substituents comprising a nitrogen, oxygen, or sulfur heteroatom.

The structure of mycolactone (Formula 1) has been unambiguously identified by multiple analytical methods including, but not limited to, proton NMR (including GMQCOSY, TOCSY, HSQC, and ROESY), and mass spectrometry. Both the observed and calculated m/z ratio by mass spectrometry (HRMS) was 765.4912 (Δ0.1 ppm). The long-range correlations between the proton signals at 2.02 and 2.41 ppm (2-$CH_2$) and the carbon signal at 173.3 ppm confirmed the position of one of the ester carbonyls at C1. The long-range coupling of olefinic methyl protons to the olefinic carbons 3 bonds away allowed the joining of spin systems separated by methyl-bearing quaternary carbons. The long-range correlations between the methyl proton signal at 1.71 ppm (22-$CH_2$) and the carbon signals at 46.4 (C7) and 123.8 ppm (C9), and the methyl proton signal at 1.64 ppm (24-$CH_3$) and the carbon signals at 44.3 (C12) and 133.9 ppm (C14), allowed the establishment of the dodecanoic chain. The long-range correlations between the olefinic protons at 5.94 (2'-CH) and 7.92 (3'-H) and the carbonyl signal at 166.0 ppm confirmed the unsaturated ester carbonyl at 1'. The olefinic proton signal at 6.35 ppm (5'-H), which is directly attached to the carbon resonating at 141.8 ppm (C5'), showed long-range correlations to carbon signals at 143.1 (C3') and 134.8 ppm (C7'), while the methyl proton signal at 1.91 ppm (19'-$CH_3$) showed long-range correlations to carbon signals at 139.9 (C9') and 134.6 ppm (C11'), respectively, completing the hexadecanoic chain. The proton signal at 4.71 ppm (5-CH) showed long-range coupling to the carbon signal at 166.9 ppm (C1') indicating that the hydroxyl function at C5 is acylated with the hexadecyl moiety. The protons on the remaining 6 hydroxyl-bearing methine functions resonated at 4.9 (C11), 4.28 (C12), 3.99 (C15'), 3.96 (C19), 3.68 (C13'), and 3.5 (C17) ppm. Based on chemical shifts, it is evident that the hydroxyl function at C11 is involved in the formation of the lactone. This was further confirmed by the presence of NOE correlations between 11-H (4.9 ppm) and 2-$CH_2$ (2.02, and 2.41 ppm) proton signals. The olefinic proton signal at 6.35 (5'-H) ppm showed NOE to proton signals due to both 17'-$CH_3$ and 18'-$CH_3$, but not to any other olefinic protons. Two isomers of the compound (designated A (major one) and B (minor one)), differing at the 4' position, were detected (Gunawardana et al., JACS 121(25): 6092–6093 (1999)). These isomers have the same biological activity.

The macrolides of Formula 2 can be made by standard, semi-synthetic techniques starting with the polyketide macrolide of Formula 1. The polyketide macrolide of Formula 1 can be isolated directly from M. ulcerans. M. ulcerans is available from at least the Trudeau Collection (Lake Saranac. N.Y. USA) and the American Type Culture Collection (ATCC), is propagated by a multiplicity of research laboratories, and can be isolated from buruli ulcers.

M. ulcerans can be propagated by any suitable means. One suitable means for propagating M. ulcerans comprises growing M. ulcerans 1615 (from the Trudeau Collection) at 32° C. in Middlebrook 7H9 medium supplemented with 0.2% (v/v) glycerol and 10% oleic acid, albumin, dextrose, and catalase enrichment (Difco). If desired, the M. ulcerans can be concentrated out of the growth medium by filtration through a 0.22 micrometer filter.

To isolate a polyketide macrolide of the present invention M. ulcerans cells were extracted with an organic solvent and subjected to a suitable purification step that separates molecules on the basis of their hydrophobicity. Any suitable organic solvent can be used for the extraction step, for example, a 2:1 mixture of chloroform and methanol or other solvents with a comparable dielectric constant, effectively extracts mycolactone and other polyketide macrolides of the present invention in about four hours with stirring. Insoluble components and hydrophilic moieties can usefully be separated from the extract by centrifugation and by adding a small volume of water (e.g., about 0.1 to about 1.0 volume) in order to facilitate phase separation. Any suitable technique for separating molecules based on their hydrophobicity, for example, silica-gel based thin layer chromatography or reverse phase liquid chromatography (e.g., reverse phase HPLC) can be used to separate the inventive polyketide macrolides from other lipophilic molecules in the extract. Advantageously, phospholipids and other co-extracted molecules can selectively be precipitated by transferring the organic extract into a solution consisting essentially of ice-cold (i.e., about 4° C.) acetone. For example, the organic solvent containing the extract can be evaporated until dry, or nearly dry, and resuspended in ice-cold acetone.

The hydrophobic separation technique results in isolation of polyketide macrolides that have an Rf of greater than 0.15 and less than 0.60 when chromatographically analyzed by silica-gel thin-layer-chromatography (SG-TLC) employing a solvent system of 90: 10:1 of chloroform:methanol:water. As is well-known in the art, an "Rf" is a number obtained by dividing the distance an analyte or compound travels from the origin of a TLC divided by the distance the solvent front travels past the origin. The origin is the location on a TLC at which a mixture of compounds to be separated is placed. While it may be desirable for many uses of the polyketide macrolide to isolate a composition comprising only one type of polyketide macrolide, for example mycolactone (Formula 1), mixtures polyketide macrolides are also useful in the context of the present inventive methods. Mycolactone, in the TLC system described above, has an Rf of about 0.23 (i.e., between about 0.19 and about 0.27). Other suitable polyketide macrolides of the present invention have observed Rf values of about 0.31 (i.e., between about 0.28 and about 0.35), of about 0.38 (i.e., between about 0.36 and about 0.42), of about 0.44 (i.e., between about 0.41 and about 0.48), and of about 0.54 (i.e., between about 0.49 and 0.60). All of these polyketide macrolides have 12-membered lactone rings and modifications in the side chains, have a molecular weight that is less than 1,000, such as 600–750, and fluoresce yellow at 375 nm of ultraviolet light.

Australian isolates of M. ulcerans contain high levels of a mycolactone having an Rf of about 0.40, i.e., between about 0.36 and about 0.42, a 12-membered lactone ring and a different carbon double bond pattern in the lower ester chain from the mycolactones of the formulae set forth herein. The activity level of the mycolactone found in Australian isolates is about 10,000-fold lower than the other mycolactones described herein. Mass spectroscopy data indicate that this mycolactone (designated mycolactone C) has a molecular mass of 728, whereas the mycolactones of formula 1 have a molecular mass of 743. Proton NMR data of mycolactone C indicate that it is identical to mycolactones A and B in the lactone portion of the molecule, with differences occurring in the side chain.

The polyketide macrolides of the present invention are susceptible to molecular damage induced by prolonged exposure to light. For example, if a polyketide macrolide is maintained at room temperature for about one week or so, an approximate 50% reduction in activity will be realized. Accordingly, the polyketide macrolide or mixtures thereof can be isolated and provided in a sterile, aseptic solution suitable for administration to humans and to other mammals in order to preserve bioactivity. The mixture can be packaged in light-resistant bottles meeting U.S. Food and Drug Administration standards, or ISO standards for the shipment of light-sensitive bottles. Preferably, the bottle or container is labeled with a label indicating the concentration of polyketide macrolides in the mixture and, optionally, a date of preparation or manufacture. Advantageously, the polyketide macrolide can be provided in a pharmaceutically acceptable carrier (described below) in order to facilitate accurate administration of precise quantities of the polyketide macrolide to mammals and to achieve beneficial pharmacodynamics.

The present invention provides in vivo and in vitro methods for selectively enriching a mixed population of fibroblasts and epithelial cells for epithelial cells. This embodiment of the present inventive method comprises administering a suitable quantity of a polyketide macrolide to the mixed population of cells and maintaining the cells under normal growth or maintenance conditions. The population is enriched in epithelial cells because fibroblasts are particularly sensitive to the polyketide macrolide, whereas epithelial cells are relatively resistant to the effects of the polyketide macrolide. When this method is carried out in vitro, it is possible to obtain a substantial enrichment in epithelial cells (e.g., at least about a 5-fold enrichment) and when the method is carried out in vivo in mammalian skin, the action of the polyketide macrolide is usually observed as an ulcer resembling a buruli ulcer.

The present invention also provides a method of inhibiting cancer in a mammal in need thereof, such as a human, including, for example, melanoma, lung cancer, breast cancer, central nervous system cancer, and other types of cancer. By "inhibiting" is meant the inhibition of further growth of an existing tumor, further expansion of cancerous cells, or metastasis. While complete inhibition is desirable, any degree of inhibition is beneficial to the mammal being treated in accordance with the method. In this embodiment of the present invention, cancer is inhibited by administering to the mammal an effective amount of a polyketide macrolide or an aseptic mixture of polyketide macrolides as described herein, whereupon the cancer in the mammal is inhibited.

The present invention also provides a method of suppressing an inflammatory response in a mammal, such as a human. The method comprises administering to a mammal an effective amount of a polyketide macrolide or an aseptic mixture of polyketide macrolides as described herein, whereupon the inflammatory response in the mammal is suppressed. By "suppressing" is meant the suppression of the inflammatory response. While complete suppression is desirable, any degree of suppression is beneficial to the mammal being treated in accordance with the method. Desirably, the polyketide macrolide or mixture thereof is present in an effective concentration at the site of inflammation. Sites of inflammation typically include injuries or wounds, the loci of inflammatory autoimmune diseases (for example, but not limited to, the joints and connective tissues of mammals afflicted with rheumatoid arthritis), and sites of infection. Desirably, suppression of the inflammatory response is manifested by a decreased number of polymorphonuclear neutrophils, preferably a substantial decreased number, i.e., at least about 100-fold reduction in the number of polymorphonuclear neutrophils, that accumulate at a site of inflammation in an untreated, but otherwise identical, mammal, such as within the first 24 hours of treatment, when the treatment occurs at approximately the same time as the cause for the inflammatory response. Alternatively, the method reduces the number of polymorphonuclear neutrophils at the site of inflammation by at least 10-fold.

The present invention also provides a method of inducing an immune response to *Mycobacteria ulcerans* without inducing a buruli ulcer. An isolate of *M. ulcerans* that produces less than about 5%, and preferably 0%, per cell of polyketide macrolides, which have an Rf of greater than 0.15 and less than 0.60 when chromatographically separated by SG-TLC employing a solvent system of 90:10:1 of chloroform:methanol:water, in comparision to a fresh culture of a virulent isolate of *M. ulcerans* 1615 is propagated. Such an isolate can be obtained in any suitable manner. One suitable method to obtain such an isolate is to propagate *M. ulcerans* on solid medium and to maintain the culture until colonies containing multiple levels of pigmentation are obtained (i.e., until the colonies have slightly discolored portions). A small number of discolored cells can be removed with an inoculating needle and propagated in isolation. These isogenic isolates surprisingly do not produce the polyketide macrolides of the present invention and are nonvirulent. The mammal, which is preferably a human, to be protected is inoculated with an immune response-inducing amount of non-virulent *M. ulcerans* cells such that the mammal has an immune response to *M. ulcerans*, which may be manifest by the appearance of a granuloma, and does not develop a buruli ulcer. The non-virulent *M. ulcerans* can optionally be killed or attenuated prior to inoculation, although the non-lethal pathology of non-attenuated *M. ulcerans* is mild enough that such attenuation is not required for safety. The determination of an immune response-inducing amount is within the ordinary skill in the art. Desirably, the mammal treated in accordance with this method is more resistant to the development of a buruli ulcer upon subsequent exposure to *M. ulcerans* than an untreated, but otherwise identical, mammal.

The polyketide macrolide, or aseptic mixture of polyketide macrolides, can be administered to a mammal in any suitable manner. For example, the polyketide macrolide can be administered to a mammal orally, via inhalation, parenterally, topically, subcutaneously, intravenously, intramuscularly, intraperitoneally, rectally, and vaginally. Preferably, the route of administration is selected to maximize the exposure to the afflicted portion e.g., cancerous or inflamed portion, of the mammal's body and to minimize systemic or widespread distribution of the polyketide macrolide to non-affected regions of the mammal's body in the method of inhibiting cancer and in the method of suppressing an inflammatory response. Preferred routes of administration for induction of an immune response are known in the art and include subcutaneous and intradermal routes of administration.

The dose administered to a mammal, particularly a human, in the context of the present inventive methods should be sufficient to cause the desired response. The ordinarily skilled artisan will appreciate that the dosage, the route, and the frequency of administration will vary depending upon the age, species, condition, and weight of the mammal, as well as any peculiar sensitivities of the mammal to be treated, and other variables known to those of ordinary skill in the art. Determination and adjustment of these parameters is within the skill of the ordinarily skilled clinician in the art as a matter of routine clinical development. Suitable therapeutic dosages range from about 0.10 nanograms per kilogram of body weight to 10 milligrams per kilogram of body weight, and optionally range from 1 to 100 milligrams per kilogram of body weight. The dosage desirably should achieve greater than 300 pg of the polyketide macrolide per ml of cells. Efficacious results can be achieved at a concentration of polyketide macrolide from about 3 ng/ml to about 3 µg/ml.

The polyketide macrolide can be mixed with any pharmaceutically acceptable carrier. Preferably, the pharmaceutically acceptable carrier does not consist essentially of acetone, e.g., is less than about 90% acetone. Preferably, the pharmaceutical carrier comprises an alcohol, an oil, fatty acid, or a glycol. Alternatively, the pharmaceutically acceptable carrier can comprise an aqueous solution (e.g., water) in which the polyketide macrolide is suspended, mixed, or emulsified. When aqueous solutions are used as pharmaceutically acceptable carriers, the composition preferably comprises a suspending agent. Injectable formulations are among those formulations that are suitable in the context of the present inventive methods. The requirements for effective pharmaceutical carriers for injectable compositions are well known to those of ordinary skill in the art (See, *Pharmaceutics and Pharmacy Practice*, J.B. Lippincott Company, Philadelphia. Pa. Banker and Chalmers, eds., pages 238–250, (1982), and *ASHP Handbook on Injectable Drugs*, Toissel, 4th ed., pages 622–630 (1986)). It is preferred that such injectable compositions be administered intravenously or locally, e.g., at or near the site of the cancer or the inflammation (e.g., infection or injury).

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The polyketide macrolide can be administered in a physiologically acceptable diluent, such as a sterile liquid, or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1, 3-dioxolane4-methanol, ethers, such as poly (ethyleneglycol) 400, an oil, a fatty acid, a fatty acid ester or glyceride, or an acetylated fatty acid glyceride with or without the addition of a pharmaceutically acceptable suspending agent, such as pectin, carbomers. methylcellulose, hydroxypropylmethylcellulose, or carboxymethylcellulose, or emulsifying agents and other pharmaceutical adjuvants.

Oils, which can be used in parenteral formulations include petroleum and animal, vegetable and synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

All formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Topical formulations are well-known to those of ordinary skill in the art and are suitable in the context of the present invention. Such formulations are typically applied to the skin or other body surfaces.

Formulations suitable for oral administration can consist of (a) liquid solutions, such as an effective amount of the polyketide macrolide dissolved or suspended in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol benzyl alcohol, and the polyethylene alcohols, either with or without the addition of a pharmaceutically acceptable suspending agent or emulsifying agent. Capsule forms can be of the ordinary hard- or soft-shelled gelatin type containing, for example, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

In view of the above, the present invention further provides a composition comprising *M. ulcerans* cells that produce less than about 5%, preferably 0%, of polyketide macrolides per cell in comparison to a fresh culture of a virulent isolate of *Mycobacteria ulcerans*, wherein the polyketide macrolides have an Rf of greater than 0.15 and less than 0.60 when chromatographically separated by SG-TLC employing a solvent system of 90:10:1 of chloroform:methanol:water. *M. ulcerans* cells that produce low levels of or no amounts of polyketide macrolides can be obtained by streaking a sample of wild-type *M. ulcerans*. such as that which can be obtained from the American Type Culture Collection, onto an agar plate and selecting for spontaneous mutants. Wild-type colonies will be yellow, whereas mutant colonies will be white. The mutant colonies can be subsequently cultured and the lipids isolated and tested for mycolactone content as exemplified herein. The composition is useful to induce an immune response, and even protection upon challenge, in accordance with the present inventive method of inducing an immune response to *M. ulcerans* and as exemplified in the Examples set forth herein.

EXAMPLES

The following examples serve to illustrate the present invention and are not intended to limit its scope in any way.

Example 1

The following example demonstrates that acetone-soluble lipids partially purified from *M. ulcerans* are a powerful inhibitor of cancer.

*M. ulcerans* 1615 was grown in liquid culture at 32° C. in Middlebrook 7H9 medium supplemented with 0.2% (v/v) glycerol and 10% oleic acid, albumin, dextrose, and catalase enrichment (Difco). Intact bacteria were harvested by passing the culture through a 0.22 micrometer filter. The bacterial mass was stirred in a 2:1 mixture of chloroform and methanol to extract the lipophilic molecules. One-fifth volume of water was added to the organic solvent extract and separated by centrifugation. The organic phase was transferred to a new container and the solvent was evaporated in a rotary evaporator. The residual sample was resuspended in ice-cold acetone to prevent solubilization of phospholipids. The acetone solution was transferred to a new container and the solvent was evaporated. The residual sample was resuspended in a saline solution and tested for the ability to inhibit the growth of cancerous cells in the (U.S.) National Cancer Institute's standardized 60 cell screening activity. The sample was a potent inhibitor of cancerous cell growth. Melanoma cells were exquisitely sensitive to the activity of the sample. Advantageously, the cytotoxic effects of the sample are reversible during the first 48 to 72 hours. After longer exposure, the cells are committed to death via the apoptotic pathway and the cells will die, even if the polyketide macrolide is subsequently removed. This property can be usefully exploited by the skilled artisan to treat selectively cancer cells over non-neoplastic cells, optionally in the context of combination chemotherapy with other known anticancer drugs. Alternatively, an apoptosis inhibitor can be administered in conjunction with the polyketide macrolide, in which case the cells die by necrosis instead of apoptosis.

Example 2

The following example demonstrates that purified mycolactone, a polyketide macrolide of the present invention, is a potent inhibitor of the growth of H460 lung cancer cells, MCF-7 breast cancer cells, and SF-268 central nervous system cancer cells. This example also demonstrates that a polyketide macrolide of the present invention having an Rf of about 0.23 by SG-TLC developed in 90:10:1 chloroform:methanol:water is a potent inhibitor of cancer cell growth.

Acetone-soluble lipids (ASLs) were prepared from intact *M. ulcerans* cells as in Example 1, except that the acetone resuspension was applied to a preparative TLC plate to allow substantial separation of the ASLs based on relative mobility in the TLC system. The ASL with a mobility of 0.23 relative to the solvent front was scraped from the plate and resuspended. Testing performed by the National Cancer Institute revealed a relative growth rate of −72%, −78%, and −79% for H460 lung cancer cells, MCF-7 breast cancer cells, and SF-268.central nervous system cancer cells, respectively.

Example 3

This example demonstrates that the major ASLs of *M. ulcerans* with Rfs of greater than 0.27 and less than 0.61 have biological and chemical properties analogous to mycolactone.

The ASLs with Rfs of greater than 0.27 and less than 0.60 were purified in the same manner as mycolactone, as described in Example 2. Proton NMR demonstrated that each major ASL was a polyketide macrolide of analogous structure to mycolactone. One ASL, a polyketide macrolide of the present invention, is structurally related to mycolactone except that it lacks two hydrogen atoms. Another ASL of the present invention is structurally related to mycolactone except that it lacks two hydrogen atoms and an oxygen atom. Loss of the two hydrogen atoms and an oxygen atom allows an epoxide to form between the 12' and 13', between the 13' and 15', or between the 17' and 19' carbon atoms. Of course, in these instances, two R groups and one of the oxygens to which they would be attached are not present in the molecule. Moreover, cytopathological assays, including the ability to inhibit the growth of murine fibroblasts and cause buruli-like skin lesions in guinea pigs, revealed that mycolactone and the other polyketide macrolides of the present invention are structurally and functionally analogous.

Example 4

This example demonstrates that mycolactone and the other polyketide macrolides of the present invention are potent inhibitors of inflammatory reactions.

Mycolactone was purified as in Example 2. Hartley guinea pigs were inoculated with an infectious quantity of *M. marinum*. When the inoculum was not accompanied by mycolactone, a painful, purulent lesion developed in the guinea pigs, indicative of an inflammatory reaction. In contrast, when mycolactone was injected into the locus, tissue necrosis still developed, but the infiltration of macrophages and polymorphonuclear neutrophils was delayed by 24 to 48 hours, resulting in greater than a 1,000-fold reduction in the number of neutrophils invading the site of infection 16 hours after infection. Inflammation, or the lack thereof, was confirmed by histopathological examination of paraffin embedded tissues stained with eosin and hematoxylin. While not desiring to be bound by any particular theory, it is believed that the subsequent inflammation that occurred in mycolactone-treated animals was partially a consequence of the continued growth of *M. marinum*. When the polyketide macrolides of the present invention are used to decrease inflammation at a site of infection, the inventive method is optionally accompanied by the administration of antibiotics. This example shows that mycolactone and other polyketide macrolides of the present invention are potent anti-inflammatory agents.

Example 5

This example demonstrates that *M. ulcerans* that produce less than about 5% of polyketide macrolides per cell in comparison to a fresh culture of a virulent isolate of *M. ulcerans* can be used to induce an immune response in a mammal to *M. ulcerans* without inducing a buruli ulcer.

Four mycolactone-negative isogenic mutants of *M. ulcerans*, namely 1615A, 1615B. 1615D (has a growth defect at stationary phase of cell cycle) and 1615E, were isolated and are available from Dr. Pamela L. C. Small, Rocky Mountain Laboratories, National Institutes of Health, Hamilton, Mont. USA. Guinea pigs were vaccinated with 1615E. Six weeks later, the guinea pigs were challenged with the corresponding parental virulent strain by injection into shaved skin on the back of the neck. Non-vaccinated control animals developed buruli ulcers following injection with the virulent parental strain, whereas none of the vaccinated animals developed ulcers. Thus, the mycolactone-negative mutant conveyed protective immunity to infection, i.e., protection upon challenge, with *M. ulcerans*.

All of the references cited herein, including patents, patent applications, literature publications, and the like, are hereby incorporated in their entireties by reference.

While this invention has been described with an emphasis upon preferred embodiments, it will be obvious to those of ordinary skill in the art that variations of the preferred compounds and methods may be used and that it is intended that the invention may be practiced otherwise than as specifically described herein.

Accordingly, this invention includes all modifications encompassed within the spirit and scope of the invention as defined by the following claims.

While this invention has been described with emphasis upon preferred embodiments, it will be obvious to those of ordinary skill in the art that the preferred embodiments may be varied. It is intended that the invention may be practiced otherwise than as specifically described herein. Accordingly, this invention includes all modifications encompassed within the spirit and scope of the appended claims.

What is claimed is:

1. An isolated polyketide macrolide of the formula:

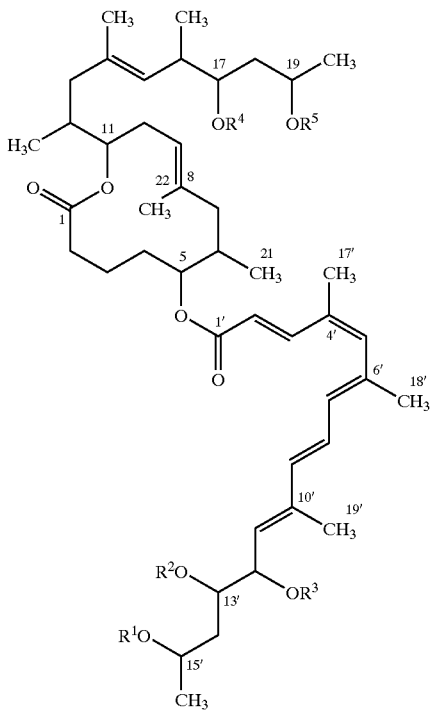

wherein $R^1$–$R^5$ are the same or different and each is independently selected from the group consisting of hydrogen, $R^6$, a $C(O)R^7$, a $C(S)R^7$, a $C(O)NHR^7$, and a $C(S)NHR^7$, wherein each occurrence of $R^6$ is independently selected from the group consisting of a $C_1$–$C_6$ alkyl, a $C_5$–$C_{12}$ aryl, and a sugar, wherein the sugar is selected from the group consisting of a tetrose, a pentose, a hexose, a heptose, a disaccharide of any of the foregoing, and a polysaccharide of any of the foregoing, where in each occurrence of $R^7$ is independently selected from the group consisting of hydrogen, a $C_1$–$C_6$ alkyl, and a $C_5$–$C_{12}$ aryl, and wherein $R^1$ and $R^2$, $R^2$ and $R^3$, and/or $R^4$ and $R^5$ can be taken together to form a ketal ring.

2. The isolated polyketide macrolide of claim 1 having the structure

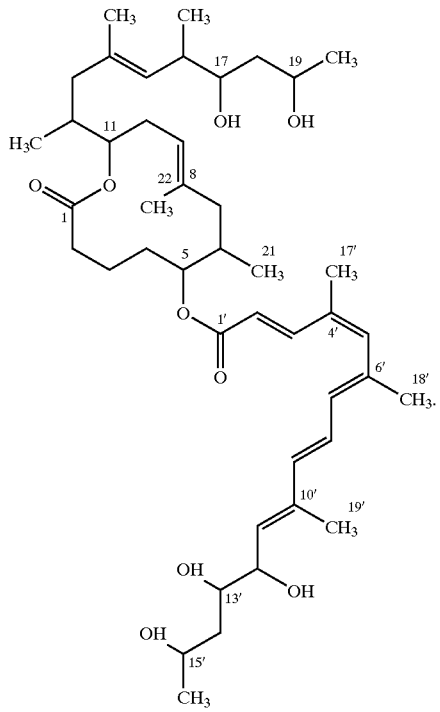

3. An aseptic mixture of polyketide macrolides comprising (i) a polyketide macrolide isolated from *Mycobacteria ulcerans* wherein the fraction corresponding to the distance the polyketide macrolide travels from the origin divided by the distance the solvent front travels past the origin (Rf) is greater than 0.15 and less than 0.60 when chromatographically separated by silica-gel thin-layer-chromatography (SG-TLC) employing a solvent system of 90:10:1 of chloroform:methanol:water and (ii) a pharmaceutically acceptable carrier.

4. The aseptic mixture of claim 3, wherein said mixture comprises mycolactone.

5. The aseptic mixture of claim 4, wherein said mixture comprises mycolactone and mycolactone is the only polyketide macrolide in said mixture.

6. The aseptic mixture of claim 3, wherein said mixture comprises a polyketide macrolide that has an Rf of from about 0.19 to about 0.27 when chromatographically separated by SG-TLC employing a solvent system of 90:10:1 of chloroform:methanol:water.

7. The aseptic mixture of claim 3, wherein said mixture comprises a polyketide macrolide that has an Rf of from about 0.28 to about 0.35 when chromatographically separated by SG-TLC employing a solvent system of 90:10:1 of chloroform:methanol:water.

8. The aseptic mixture of claim 3, wherein said mixture comprises a polyketide macrolide that has an Rf of from about 0.36 to about 0.42 when chromatographically separated by SG-TLC employing a solvent system of 90:10:1 of chloroform:methanol:water.

9. The aseptic mixture of claim 3, wherein said mixture comprises a polyketide macrolide that has an Rf of from about 0.41 to about 0.48 when chromatographically separated by SG-TLC employing a solvent system of 90:10:1 of chloroform:methanol:water.

10. The aseptic mixture of claim 3, wherein said mixture comprises a polyketide macrolide that has an Rf of from about 0.49 to about 0.60 when chromatographically separated by SG-TLC employing a solvent system of 90:10:1 of chloroform:methanol:water.

11. The aseptic mixture of claim 3, wherein the pharmaceutically acceptable carrier comprises a compound selected from the group consisting of an alcohol, an oil, a fatty acid, and a glycol.

12. The aseptic mixture of claim 3, wherein the mixture comprises water.

13. The aseptic mixture of claim 3, wherein the mixture comprises acetone in an amount less than 90% by volume.

14. The aseptic mixture of claim 3, wherein the mixture is stored in a light-resistant container.

15. A method of inhibiting cancer in a mammal in need thereof, comprising administering to said mammal an effective amount of the isolated polyketide macrolide of claim 1, whereupon the cancer in the mammal is inhibited.

16. A method of inhibiting cancer in a mammal in need thereof, comprising administering to said mammal an effective amount of the aseptic mixture of macrolides of claim 3, whereupon the cancer in the mammal is inhibited.

17. The method of claim 15, wherein said cancer is melanoma, lung cancer, breast cancer, or central nervous system cancer.

18. A method of suppressing an inflammatory response in a mammal, comprising administering to said mammal an effective amount of the isolated polyketide macrolide of claim 1, whereupon the inflammatory response in the mammal is suppressed.

19. A method of suppressing an inflammatory response in a mammal, comprising administering to said mammal an effective amount of the aseptic mixture of macrolides of claim 3, whereupon the inflammatory response in the mammal is suppressed.

20. The method of claim 18, wherein suppression of said inflammatory response is manifested by a decreased number of polymorphonuclear neutrophils at a site of inflammation by comparison to an untreated, but otherwise identical, mammal.

21. A method of inducing an immune response to *Mycobacteria ulcerans* without inducing a buruli ulcer comprising inoculating a mammal with an immune response-inducing amount of *Mycobacteria ulcerans* cells that produce less than about 5% of polyketide macrolides per cell in comparison to a fresh culture of a virulent isolate of *Mycobacteria ulcerans* 1615, wherein said polyketide macrolides have an Rf of greater than 0.15 and less than 0.60 when chromatographically separated by SG-TLC employing a solvent system of 90:10:1 of chloroform: methanol:water, whereupon an immune response to *M. ulcerans* is induced in said mammal without induction of a buruli ulcer.

22. The method of claim 21, wherein said mammal is a human.

23. A composition comprising *Mycobacteria ulcerans* cells that produce less than about 5% of polyketide macrolides per cell in comparison to a fresh culture of a virulent isolate of *Mycobacteria ulcerans* 1615, wherein said polyketide macrolides have an Rf of greater than 0.15 and less than 0.60 when chromatographically separated by SG-TLC employing a solvent system of 90:10:1 of chloroform:methanol:water.

24. The composition of claim 23, wherein the *M. ulcerans* cells produce 0% polyketide macrolides per cell.

25. A method of inhibiting cancer in a mammal in need thereof, comprising administering to said mammal an effective amount of the isolated polyketide macrolide of claim 2, whereupon the cancer in the mammal is inhibited.

26. The method of claim 16, wherein said cancer is melanoma, lung cancer, breast cancer, or central nervous system cancer.

27. A method of suppressing an inflammatory response in a mammal, comprising administering to said mammal an effective amount of the isolated polyketide macrolide of claim 2, whereupon the inflammatory response in the mammal is suppressed.

28. The method of claim 19, wherein suppression of said inflammatory response is manifested by a decreased number of polymorphonuclear neutrophils at a site of inflammation by comparison to an untreated, but otherwise identical, mammal.

* * * * *